United States Patent [19]
Beach et al.

[11] Patent Number: 6,042,556
[45] Date of Patent: Mar. 28, 2000

[54] METHOD FOR DETERMINING PHASE ADVANCEMENT OF TRANSDUCER ELEMENTS IN HIGH INTENSITY FOCUSED ULTRASOUND

[75] Inventors: Kirk W. Beach, Seattle, Wash.; Katherine G. Brown, Coppell, Tex.; Melani I. Plett, Bellevue; Michael J. Caps, Seattle, both of Wash.

[73] Assignee: University of Washington, Seattle, Wash.

[21] Appl. No.: 09/148,754

[22] Filed: Sep. 4, 1998

[51] Int. Cl.[7] ........................................ A61B 8/00
[52] U.S. Cl. ................................ 601/3; 600/437
[58] Field of Search ............................ 601/2, 3; 600/437; 607/96

[56] References Cited

U.S. PATENT DOCUMENTS

| | | | |
|---|---|---|---|
| 5,435,311 | 7/1995 | Umemura et al. | 128/660.03 |
| 5,558,092 | 9/1996 | Unger et al. | 128/660.03 |
| 5,657,760 | 8/1997 | Ying et al. | |
| 5,984,881 | 11/1999 | Ishibashi et al. | 601/2 |

OTHER PUBLICATIONS

Thomas et al.; "Ultrasonic Beam Focusing Through Tissue Inhomogeneities with a Time Reversal Mirror: Application to Transskull Therapy," IEEE Trans. on Ultrasonics, Ferroelectrics and Freq. Control; vol. 43, No. 6 Nov. 1996.

Crum, Lawrence A.; "An Acoustic Hemostasis Device for Advanced Trauma Care," Proposal to Advanced Research Projects Agency MURI '95 (Arlington, Va.) dated Mar. 10, 1995.

*Primary Examiner*—William E. Kamm
*Assistant Examiner*—Eleni Mantis Mercader
*Attorney, Agent, or Firm*—Steven P. Koda

[57] ABSTRACT

Phase of each transducer element of a high intensity focused (HIFU) transducer array is controlled to compensate for phase change introduced by varying velocity through differing tissue along a path towards a treatment volume. The echo of a specific harmonic of ultrasound pulses of moderate intensity and less than HIFU intensity are used to measure the propagation path transit time of each HIFU transducer element that will converge in a treatment volume through nonhomogeneous tissue. The moderate intensity is outside the linear region between molecular velocity fluctuations and pressure fluctuations. Thus, specific harmonic echoes are distributed in all directions from the treatment volume. Temporal delay in the specific harmonic echoes provide a measure of the propagation path transit time to transmit a pulse that will converge on the treatment volume.

25 Claims, 10 Drawing Sheets

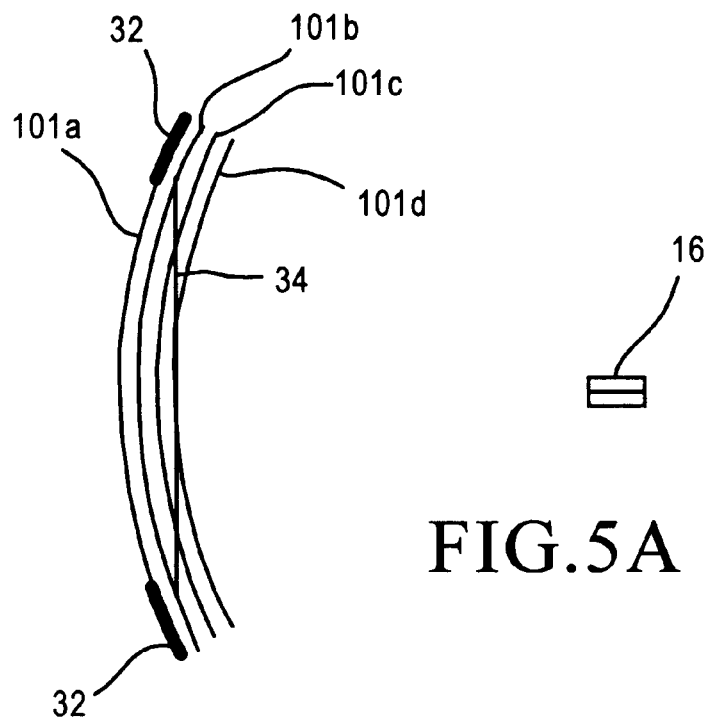
FIG.5A
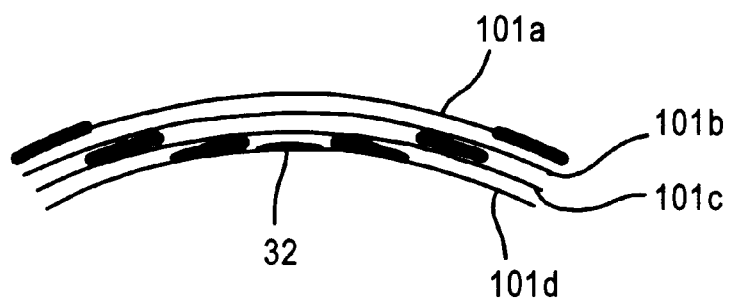
FIG.5B

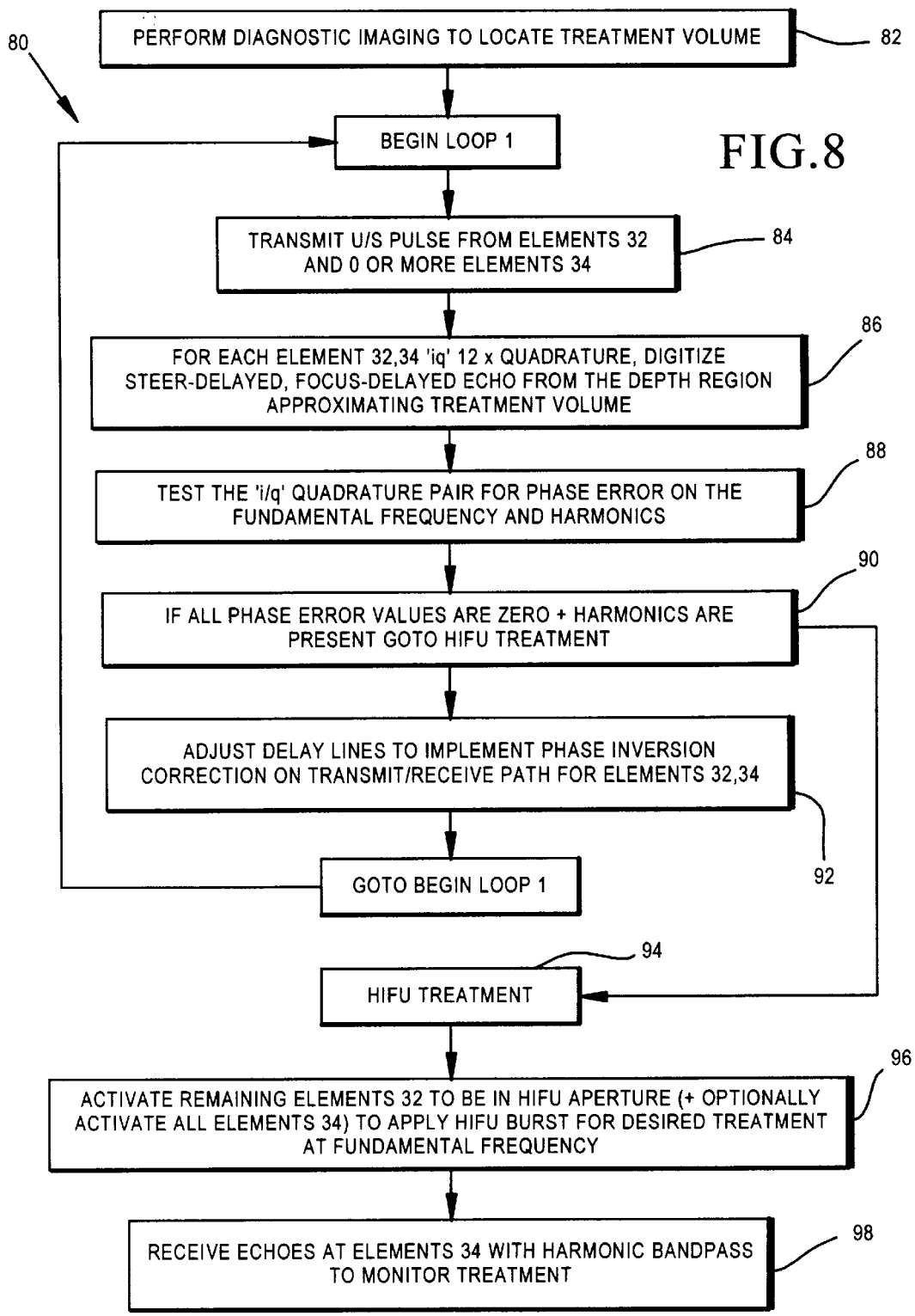

FIG.9B

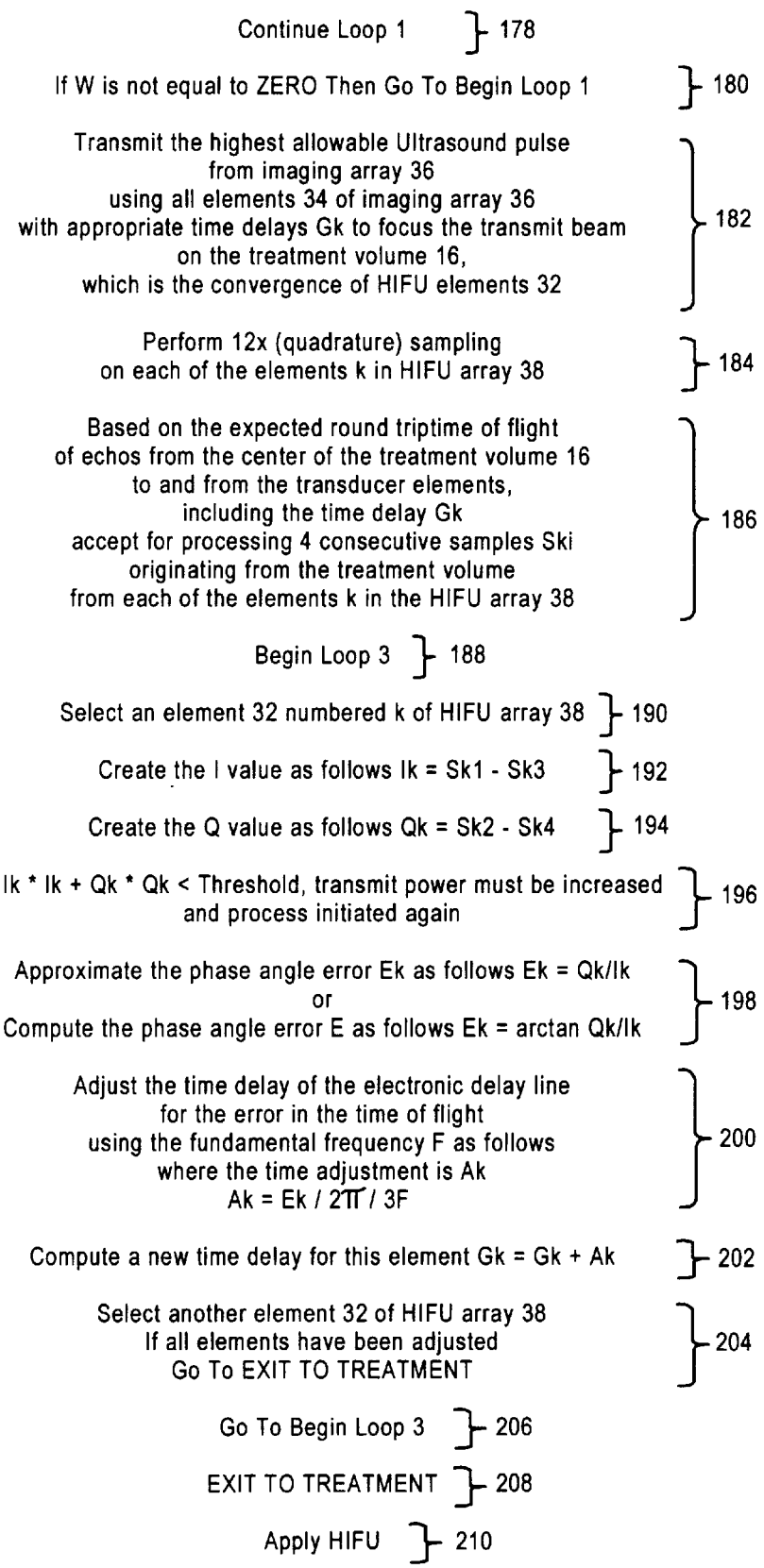

Continue Loop 1 — 178

If W is not equal to ZERO Then Go To Begin Loop 1 — 180

Transmit the highest allowable Ultrasound pulse
from imaging array 36
using all elements 34 of imaging array 36
with appropriate time delays Gk to focus the transmit beam
on the treatment volume 16,
which is the convergence of HIFU elements 32 — 182

Perform 12x (quadrature) sampling
on each of the elements k in HIFU array 38 — 184

Based on the expected round triptime of flight
of echos from the center of the treatment volume 16
to and from the transducer elements,
including the time delay Gk
accept for processing 4 consecutive samples Ski
originating from the treatment volume
from each of the elements k in the HIFU array 38 — 186

Begin Loop 3 — 188

Select an element 32 numbered k of HIFU array 38 — 190

Create the I value as follows $Ik = Sk1 - Sk3$ — 192

Create the Q value as follows $Qk = Sk2 - Sk4$ — 194

If $Ik * Ik + Qk * Qk$ < Threshold, transmit power must be increased
and process initiated again — 196

Approximate the phase angle error Ek as follows $Ek = Qk/Ik$
or
Compute the phase angle error E as follows $Ek = \arctan Qk/Ik$ — 198

Adjust the time delay of the electronic delay line
for the error in the time of flight
using the fundamental frequency F as follows
where the time adjustment is Ak
$Ak = Ek / 2\pi / 3F$ — 200

Compute a new time delay for this element $Gk = Gk + Ak$ — 202

Select another element 32 of HIFU array 38
If all elements have been adjusted
Go To EXIT TO TREATMENT — 204

Go To Begin Loop 3 — 206

EXIT TO TREATMENT — 208

Apply HIFU — 210

METHOD FOR DETERMINING PHASE ADVANCEMENT OF TRANSDUCER ELEMENTS IN HIGH INTENSITY FOCUSED ULTRASOUND

FEDERAL FUNDING STATEMENT

This invention was made with government support under grant number N0001496-1-0630 awarded by the United States Navy. The government has certain rights in the invention.

BACKGROUND OF THE INVENTION

This invention relates generally to the use of ultrasonics in medical technology applications, and more particularly to a method and apparatus for applying high intensity focused ultrasound through nonhomogeneous volumes.

Sound waves that have a frequency greater than approximately 20 kHz are referred to as ultrasound. Much of the research and development in the field of medical ultrasound relates to diagnostic applications and therapeutic applications. Medical diagnostic ultrasound systems are useful for generating images of anatomical structures within a patient's body. The images are obtained by scanning a target area with waves of ultrasound pulses. In therapeutic ultrasound applications, high intensity ultrasound pulses are transmitted into a target area to induce changes in state of the target. High intensity ultrasound pulses induce changes in state through thermal effects (e.g., induced hyperthermia) and mechanical effects (e.g., induced cavitation).

In medical ultrasound applications, ultrasound pulses are delivered to a patient by an ultrasound transducer. To obtain the ultrasound pulses, electronic signals are input to the transducer. The transducer then converts the electrical signals into ultrasound pulses which are transmitted into the patient's body as an ultrasound beam. Such ultrasound beam is absorbed, dispersed, and reflected. Diagnostic applications take advantage of the reflected ultrasound energy, which is analyzed and processed to generate image and flow information. Therapeutic applications take advantage of the absorbed ultrasound energy to change the state of a target area. Dispersion is an aspect of ultrasound technology that poses challenges to be overcome. Specifically in therapeutic applications, it is desired that ultrasound energy cause a change of state at the target area and not adversely impact other volumes within the patient. Refractive dispersion diminishes the therapeutic effect of ultrasound energy and causes the ultrasound energy to be absorbed at unintended areas. Accordingly there is a need for accurately focussing the HIFU beam.

In a hyperthermia HIFU treatment the ultrasound beam is highly focused. The beam intensities increase along the beam path from the transducer to the target area. At the target area very high temperatures can be induced. The absorption of the ultrasound energy at the target area induces a sudden temperature rise (e.g., tens of degrees centigrade per second). This temperature rise causes coagulation or ablation of target area cells. Accordingly, hyperthermia HIFU treatments can cause damage to an internal lesion. It is desirable that such damage occur without harming intermediary cells between the transducer and the target area.

HIFU treatments are desired for rapid heating of human tissues to arrest bleeding and to ablate tumors. Typically, a target area is located deep in the body and the ultrasound energy is delivered through the skin. Using an intensity in excess of 1000 W/cm$^2$ spatial peak continuous wave (SPCW), the target area is heated at a rate of approximately 25° C./second. To limit the rapid heating effects to the desired target area, and spare the intervening tissue, a large aperture transducer is used. Along the path to the target area, however, the ultrasound energy travels through fat and muscle, (i.e., the ultrasound travels through a nonhomogeneous medium). The ultrasound travels at different speeds through the different materials resulting in refractive dispersion of the ultrasound pulses. This causes difficulty in focusing to the desired target area. This invention is directed to improving focus of high intensity ultrasound through nonhomogeneous tissue so that (i) thermal effects in intermediary tissue are controlled and harmless, and (ii) an effective therapeutic dose is delivered to the target volume.

The intensities described in this application are specified as spatial peak continuous wave (SPCW), spatial peak temporal average (SPTA), or spatial peak temporal peak (SPTP). Referring to FIG. 1A, a SPCW waveform 21 is shown. The dotted portion 23 indicates negative pressures which are cut off. Conventional diagnostic ultrasound applications use ultrasound pulses with intensities of up to 100 mW/cm$^2$ spatial peak temporal average (SPTA) as exemplified by waveform 25 of FIG. 1B. The dotted portion 27 indicates negative pressures which are cut off. Referring to FIG. 1C, a SPTA waveform 29 is shown. Each of these waveforms 21, 25, 29 are for a 1 MHz ultrasound waveform.

SUMMARY OF THE INVENTION

According to the invention, the phase of each transducer element of a high intensity focused ultrasound (HIFU) transducer array is controlled to compensate for phase change introduced by differing tissue along a path towards a treatment volume.

Conventional diagnostic ultrasound applications use ultrasound pulses with intensities of up to 100 mW/cm$^2$ spatial peak temporal average (SPTA). HIFU applications use ultrasound pulses with intensities of about 1000 W/cm$^2$ SPCW (i.e., about 10,000 times greater). According to an aspect of this invention, an aiming aperture array momentarily generating 10,000 mW/cm$^2$ spatial peak temporal peak (SPTP) at the target volume (i.e., about the maximum diagnostic intensity and about 1000 times less than HIFU intensities) is used for determining path length for each element of a transducer array between the transducer head and treatment volume. In diagnostic applications using intensities of 100 mW/cm$^2$ SPTP sinusoidal pressure fluctuations are approximately 0.6 atmospheres. Thus, the highest instantaneous pressure in tissue is between 0.4 atm and 1.6 atm. At these intensities, a linear relationship exists between molecular velocity fluctuations and pressure fluctuation. At 300 mW/cm$^2$ SPTP the pressure variation is 1.0 atm. Thus, the highest instantaneous pressure at such intensity is between 0.0 atm and 2.0 atm. Within this pressure range, there still is a linear relationship between molecular velocity fluctuations and pressure fluctuations. The 300 mW/cm$^2$ SPTP intensity is called the threshold intensity. Further increases in intensity cannot drive the lower limit negative. As a result, at higher intensities the pressure wave becomes clipped, introducing harmonics into the pressure fluctuations. Echoes from the lower intensity regions will contain only the fundamental frequency, whereas echoes from the target volume (i.e., a high intensity region) will contain the fundamental frequency and its harmonics.

Because the ultrasound transducer is sensitive to the odd harmonics, a specific harmonic, such as the third harmonic echo of an ultrasound pulse, is used to measure propagation path transit time. A moderate power intensity, greater than the threshold intensity (300 mW/cm² SPTP) and less than HIFU intensity (1000 W/cm² SPCW), is used. The propagation path transit time is measured for each transducer element's pulse that will converge in a treatment volume through nonhomogeneous tissue. The moderate power level 10 W/cm² SPTP is not enough to be considered HIFU and will be affected by refractive aberration by, for example, subcutaneous fat, along the path between the transducer and the treatment volume. Although such aberration will defocus the beam, decreasing the intensity at the treatment volume, the moderate intensity must be above the threshold value so that harmonics are generated in and radiated from the treatment volume. Because the 100 W/cm² SPTP power level is above the linear region between molecular velocity fluctuations and pressure fluctuations, the echoes at the specific harmonic used are distributed in all directions from the treatment volume. These harmonics are coherent with the fundamental frequency. Thus, the temporal delay in the specific harmonic echoes observed by each transducer element, such as the third harmonic echoes, provides a measure of the propagation path transit time that will be experienced by the corresponding portion of the transmitted HIFU ultrasound, if it is to converge on the treatment volume.

According to a method of this invention, a diagnostic ultrasound imaging transducer array is used to identify and locate a treatment volume to be treated with HIFU energy. A high power test aperture including imaging transducer elements then is used to focus on the treatment volume and deliver a super threshold test pulse. At another step echoes at a specific harmonic, such as the third harmonic, are received by all elements of an enlarged high intensity aperture. Phase is measured for each element. A phase inversion delay then is computed for each element. At another step the enlarged high intensity aperture is used to apply high intensity ultrasound energy focused to the treatment volume.

According to another aspect of the invention, pitch between transducer elements is prescribed to be finer than the spatial frequency of undulations of subcutaneous fat. As ultrasound energy passes through subcutaneous fat refractive aberration occurs. Such subcutaneous fat typically is undulated in a wave-like shape having different thicknesses at different areas. By spacing the transducer elements at a pitch finer than the spatial frequency of these undulations, the variations in transit time along each of the ultrasound trajectory paths from each individual transducer element to the commmon treatment volume can be compensated by electronic delay lines, one located between each transducer element and the common HIFU transmitter, so that the transit time along each path consisting of the delay line, the transducer element, and the tissues (interposed fat, muscle and other tissues), between the common HIFU transmitter and the common treatment volume is identical.

According to another aspect of the invention, the power delivered to select elements of the transducer array is adjusted to improve the convergence of power on the treatment volume. The select elements are the transducer elements terminating a path from the treatment volume where the ultrasound has been subject to excessive attenuation.

According to another aspect of the invention, select elements of a transducer array overlaying a patient's ribs are deactivated to avoid bone heating, without degrading the effectiveness of other transducer elements emitting ultrasound toward the treatment volume.

During a HIFU treatment, ultrasound energy is applied through a nonhomogeneous mass to a treatment volume. Application of the ultrasound energy causes molecular velocity fluctuation and pressure fluctuation along a path from a source of ultrasound energy to the treatment volume. There is a threshold intensity level of the applied ultrasound energy, above which a relationship between the molecular velocity fluctuations and the pressure fluctuations becomes nonlinear. The method of treatment includes, at one step, identifying a treatment volume to be treated. At another step configuring a first transducer array to define a first aperture. The first transducer array is formed by a plurality of transducer elements. While the first transducer array is configured to define the first aperture, ultrasound energy is transmitted from the first transducer array at a prescribed frequency and at a first intensity greater than the threshold intensity. Echoes of the transmitted ultrasound energy are received at the first transducer array and at a second transducer array having a plurality of transducer elements. The echoes include ultrasound energy at the prescribed frequency and at harmonics of the prescribed frequency. The phase of the echoes are compared at selected harmonics, such as the third harmonic, for each element of the first and second transducer arrays. Steering and/or focus delays for one or more elements of the transducer arrays then is adjusted to alter the phase, and optionally the amplitude, of the received echoes. Steps of transmitting, receiving, comparing and adjusting are repeated until each element of the first and second transducer array is properly aimed at the treatment volume. Such adjusting step serves for a phase inversion process in which respective propagation transit times are applied as an advance time to each corresponding transducer element. While phase inversion is applied, ultrasound energy is transmitted from the first and second transducer array to the treatment volume at a second intensity for achieving desired ultrasonic medical therapy of the treatment volume. The second intensity at the treatment volume is greater than the first intensity and is a HIFU intensity. In some embodiments the first and second transducer arrays are portions of one transducer array. In some embodiments the steering and focus delay adjustment only is performed for elements of the second transducer array.

According to one advantage of the invention, HIFU pulses are transmitted through nonhomogeneous tissue without adversely heating tissue in the path between the ultrasound transducer and the treatment volume. These and other aspects and advantages of the invention will be better understood by reference to the following detailed description taken in conjunction with the accompanying drawings.

BRIEF DESCRIPTION OF THE DRAWINGS

FIGS. 5A–B are side view diagrams of the ultrasound transducer array receiving echo wavefronts from a treatment volume;

FIG. 8 is a flow chart of a method for focussing the transducer array of FIG. 4 according to an embodiment of this invention;

FIGS. 9A–B are more detailed flow charts of a method for focussing the transducer array of FIG. 4 according to an embodiment of this invention;

DESCRIPTION OF SPECIFIC EMBODIMENTS

Overview

Figure 2:
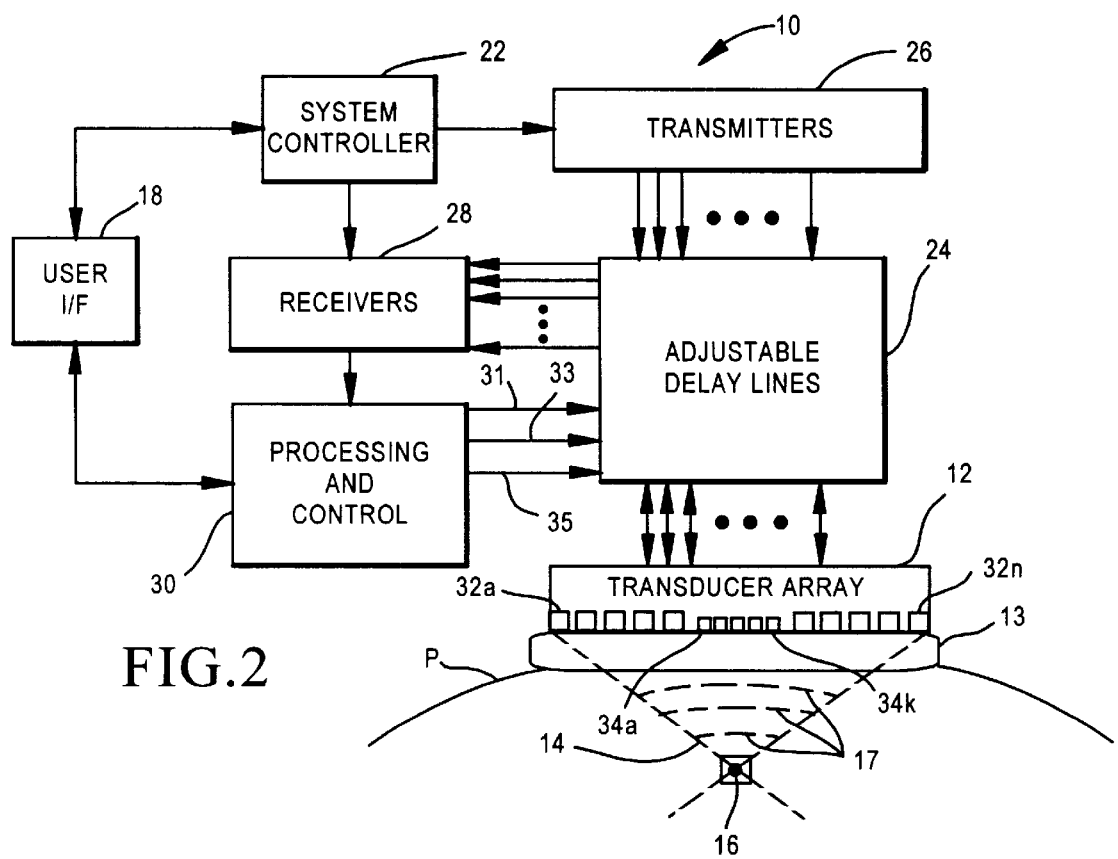
FIG. 2 is a block diagram of an ultrasound system according to an embodiment of this invention.

FIG. 2 shows a block diagram of an ultrasound system 10 for performing high intensity focused ultrasound ('HIFU') according to an embodiment of this invention. A HIFU beam 14 is emitted from a transducer array 12 and passes through an acoustic coupling pad 13 into a patient P to therapeutically act upon the patient. The ultrasound energy is in part absorbed by tissue or other physical matter along the path of the beam 14. FIG. 2 shows various wave fronts 17 of the ultrasound beam 14. The absorbed energy at the focus of the ultrasound beam causes thermal and mechanical state changes of the tissue and other physical matter in the focus region of the patient. In particular, the HIFU beam 14 induces hyperthermia and/or tissue necrosis at a desired treatment volume 16. Very high temperatures (e.g., 80° C.) are quickly induced (e.g., tens of degrees centigrade per second increases) at the treatment volume causing ablation of treatment volume cells or necrotization of an internal lesion. The ultrasound energy may be dispersed by refraction along its path to the treatment volume 16. This invention is directed toward accounting for such refractive dispersion and compensating for the dispersive effect of refraction to effectively focus the HIFU beam 14 upon the treatment volume 16 and achieve desired therapy.

The ultrasound system 10 includes a user interface 18, a system controller 22, the transducer array 12, adjustable delay lines 24, transmitters 26, receivers 28 and a processing and control unit 30. In one embodiment there is a transmit channel and a receive channel, or a transmitter 26 and a receiver 28 for each element 32, 34 of the transducer array 12. The system controller 22 serves to control the timing of the system and triggers the transmitters 26 and receivers 28. For the transmit function, the system controller generates electronic signals at desired frequencies which are input to the transmitters 26 to trigger an ultrasound burst. For a receive function the system controller triggers the receivers 28 to sample the ultrasound echoes.

Figure 3:
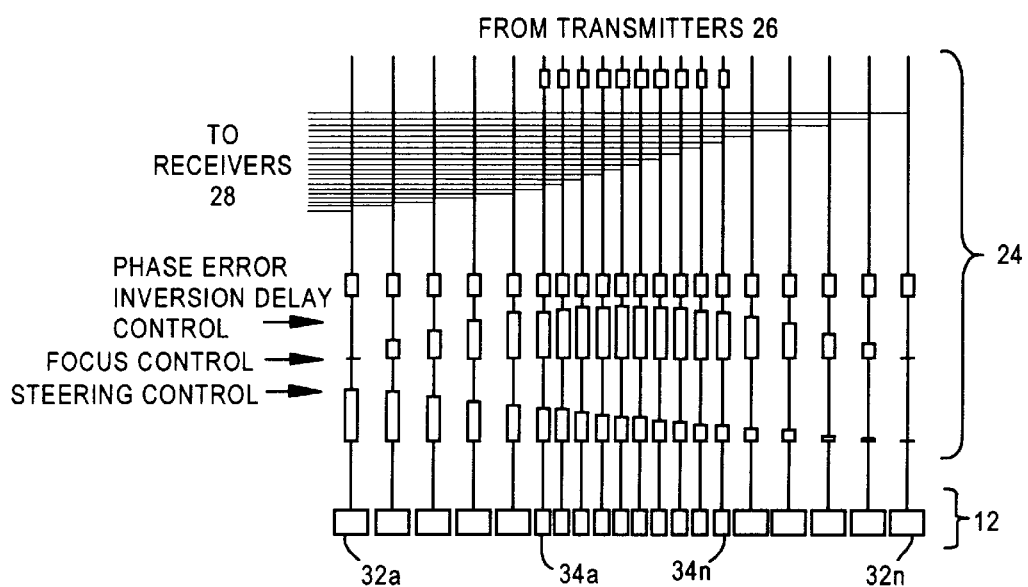
FIG. 3 is a diagram ultrasound parameter control lines for the transducer array of FIG. 2.

The transmitters 26 drive the respective elements of the transducer array 12. The receivers 28 sample the returning echoes. The transmitted ultrasound burst is controlled using delay, focus and steering controls. The received echoes are controlled using delay, focus and steering controls. In one embodiment the transmitter and receiver share a common steering control. The controls are implemented by the processing and control unit 30 and the adjustable delay lines 24. FIG. 3 shows the delay lines 24 and the transducer array 12. Pulses from the transmitters 26 travel along a respective delay line to a corresponding transducer element 32, 34. Aperture is a control of which respective transducer elements 32, 34 of array 12 are active. Thus, the aperture control determines which transducer elements are activated by the transmitter. The focus control defines respective delays for the firing of the active transducer elements. The steering control defines a beam tilt resulting from timing delays. The aperture may vary for transmission and reception. The focus and steering preferably are the same for transmission and reception. Preferably, the receiver aperture includes all transducer elements with the data for each channel processed separately.

During the calibration process of this invention, the processing and control unit 30 (see FIG. 3) adjusts the controls automatically to accurately focus the ultrasound burst on the desired treatment volume 16. Pulse echoes of ultrasound bursts are reflected back from various tissue of the patient to the ultrasound transducer array 12. The received ultrasound energy is converted into electronic signals. Aperture, focus and steering parameters determine the timing and adjustment of the electronic signals. The electronic signals are sampled at the receivers 28. The received signals are processed by the processing and control unit 30. The processing unit 30 performs signal processing analysis. In addition the processing and control unit 30 embodies conventional image processing and video processing methods for generating images to be displayed on a display device. Furthermore, the processing and control unit 30 implements software embodying a method for effectively focusing the transmitted ultrasound burst according to an embodiment of this invention. Specifically, the processing and control unit 30 provides phase error inversion adjustments to the delay lines 24. The processing unit 30 is formed by one or more microprocessors, digital signal processors, multiprocessors or other known processing unit structure. The program implementing the method of this invention adds novel configurations to the processing unit 30.

Figure 4:
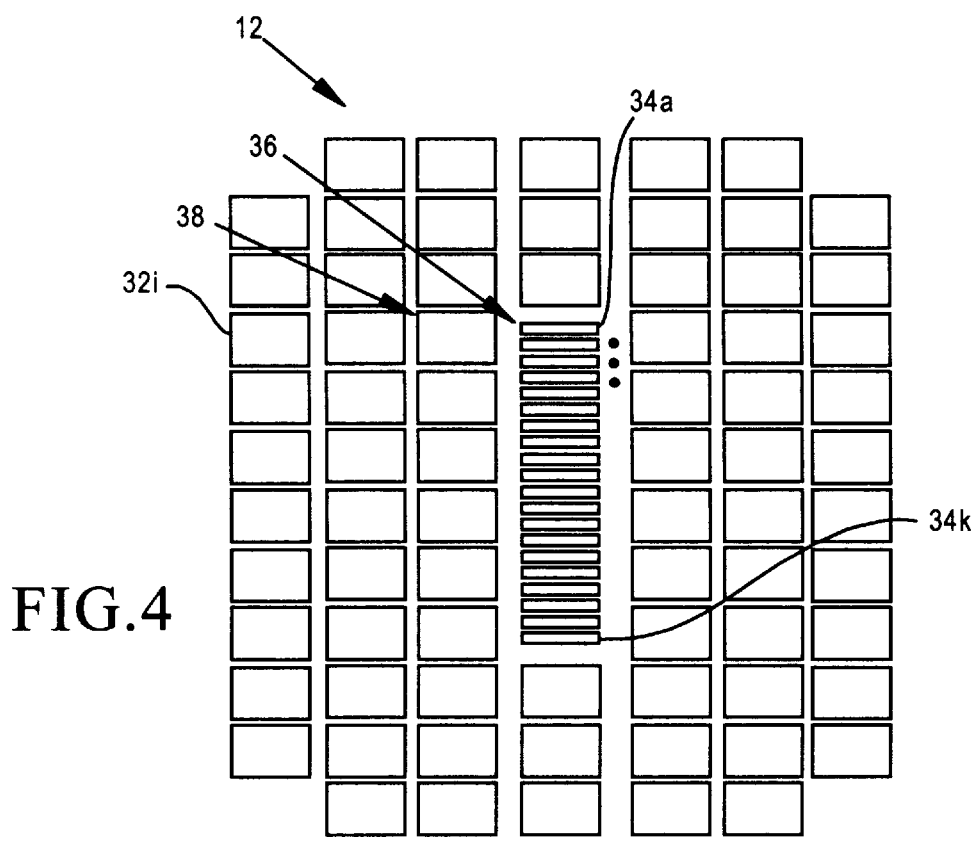
FIG. 4 is a diagram of an ultrasound transducer array layout for the transducer array of FIG. 2.

FIG. 4 shows a transducer array 12 layout according to an embodiment of this invention. The transducer array includes an imaging array portion 36 and a HIFU array portion 38 concentrically surrounding the imaging array portion 36. The imaging array portion 36 includes a plurality of transducer elements 34a through 34k. In one embodiment the imaging array portion 36 is formed by a linear transducer array. In other embodiments the imaging array portion 36 is formed by a circular, triangular or multidimensional transducer array (e.g., 1.5 dimensional array or a 2 dimensional array). The HIFU array portion 38 includes a plurality of transducer elements 32a–32n. In one embodiment the HIFU array elements 32 and the imaging array elements 34 are of the same size. In another embodiment, as shown in FIG. 4, the HIFU transducer elements 32 have a larger surface area than the imaging transducer elements 34. In an alternative embodiment the imaging transducer array portion 36 and HIFU transducer array portion 38 are separate transducer arrays having known locations relative to each other.

FIGS. 5A and 5B show the transducer array 12 along with spherical wavefronts of the ultrasound echoes received from the treatment volume 16. Note that the larger transducer elements 32 are tilted toward the treatment volume. This is preferable so that the spherical wavefronts 101a–101d cross a given transducer element 32 at a given angle. The tilt may vary for each of one or more elements 32. Phase adjustments then are made to compensate for refractive aberration.

Method for Focussing High Intensity Ultrasound Beam

High intensity ultrasound is used to oblate tissue, to coagulate blood in tissue, and to kill micro-organisms and other infective agents. The volumes treated with the high intensity ultrasound typically are deep within normal organs and tissues. A high intensity focused ultrasound beam delivers high power to a small treatment volume (e.g, cubic millimeter volume range), while sparing treatment from the surrounding tissue. One measure of treatment is referred to as exposure. Exposure equals the intensity of the ultrasound beam times the absorption rate. Exposure is to be maximized in the treatment volume and minimized in all surrounding tissues. The surrounding tissues at greatest risk from treatment harm are those superficial tissues that are between the treatment volume and the high intensity focused ultrasound transducer array 12. Secondarily at risk are those tissues on the other side of the treatment volume from the transducer array 12.

The desired effect of treatment is heating of tissue within the treatment volume 16 resulting from absorption of the high intensity ultrasound. Some of the energy absorbed is received from the propagating ultrasound beam at the insonicating frequency. Additional energy is absorbed from ultrasound propagating at harmonics of the insonicating frequency. Such harmonics occur because of the nonlinear propagation of the ultrasound beam. This causes ultrasound energy at the insonicating frequency to be converted to ultrasound energy at harmonic multiples of the insonicating frequency. Higher frequency ultrasound is absorbed at a higher rate, proportional to frequency. Thus, there is an added and beneficial heating effect from the ultrasound beam harmonics. There is relatively greater absorption at these harmonics because of the greater absorption which occurs at the higher frequencies.

To achieve maximum exposure at the treatment volume, a maximum intensity beam, as limited by the aperture, is to be achieved. Such maximum intensity is to be achieved without adversely impacting the tissue surrounding the treatment volume. Dispersion of the ultrasound beam is one source of difficulty. In particular refractive aberration due to differences in the speed of ultrasound in the most superficial tissues nearest the ultrasound transducer cause the greatest dispersive effect on the focus at the treatment volume. This invention is directed toward a method which predicts refractive dispersion of the focus of the ultrasound on the treatment volume, compensates for the predicted dispersion, and tests the resulting focus to verify that the effects have been properly compensated. As a result, exposure and harmful effect of the high frequency focused ultrasound on the surrounding tissue is minimized.

Figure 6:
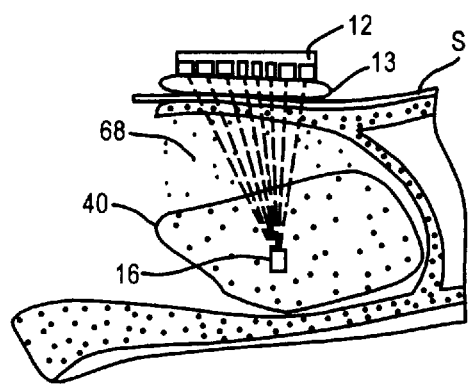
FIG. 6 is a first schematic view of a HIFU treatment to an organ.
Figure 7:
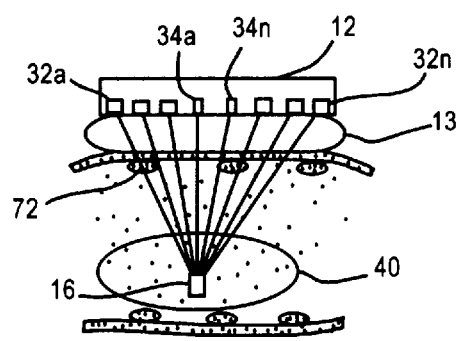
FIG. 7 is a second schematic view of the HIFU treatment of FIG. 5 showing ultrasound energy applied between the intercostal openings of a patient's rib cage.

Referring to FIGS. 6 and 7, the transducer array 12 implements a HIFU treatment of a patient's organ 40. An acoustic coupling pad 13 is positioned between the patient's skin S and the transducer array 12. Ultrasound energy travels from the transducer elements 32, 34 through the patient's skin S and through various tissues 68 toward the organ 40. The ultrasound energy focuses at the treatment volume 16. In an implementation where bone, air pockets or other ultrasound-opaque regions occur along the path between a transducer element and the treatment volume, such transducer elements are deactivated as shown in FIG. 7. Specifically, FIG. 7 shows an ultrasound beam which travels through the intercostal regions of a patient's rib cage 72. According to an aspect of this invention, the aperture of the transducer array 12 is controlled so as not to transmit energy through the ultrasound-opaque regions. This is achieved by monitoring the echoes of the transmitted ultrasound burst at each active element. If the echo amplitude to that element, when gated to the target volume, is below a threshold value, then it is assumed that the path is blocked by an ultrasound-opaque region. Such elements then are deactivated.

Figure 9A:
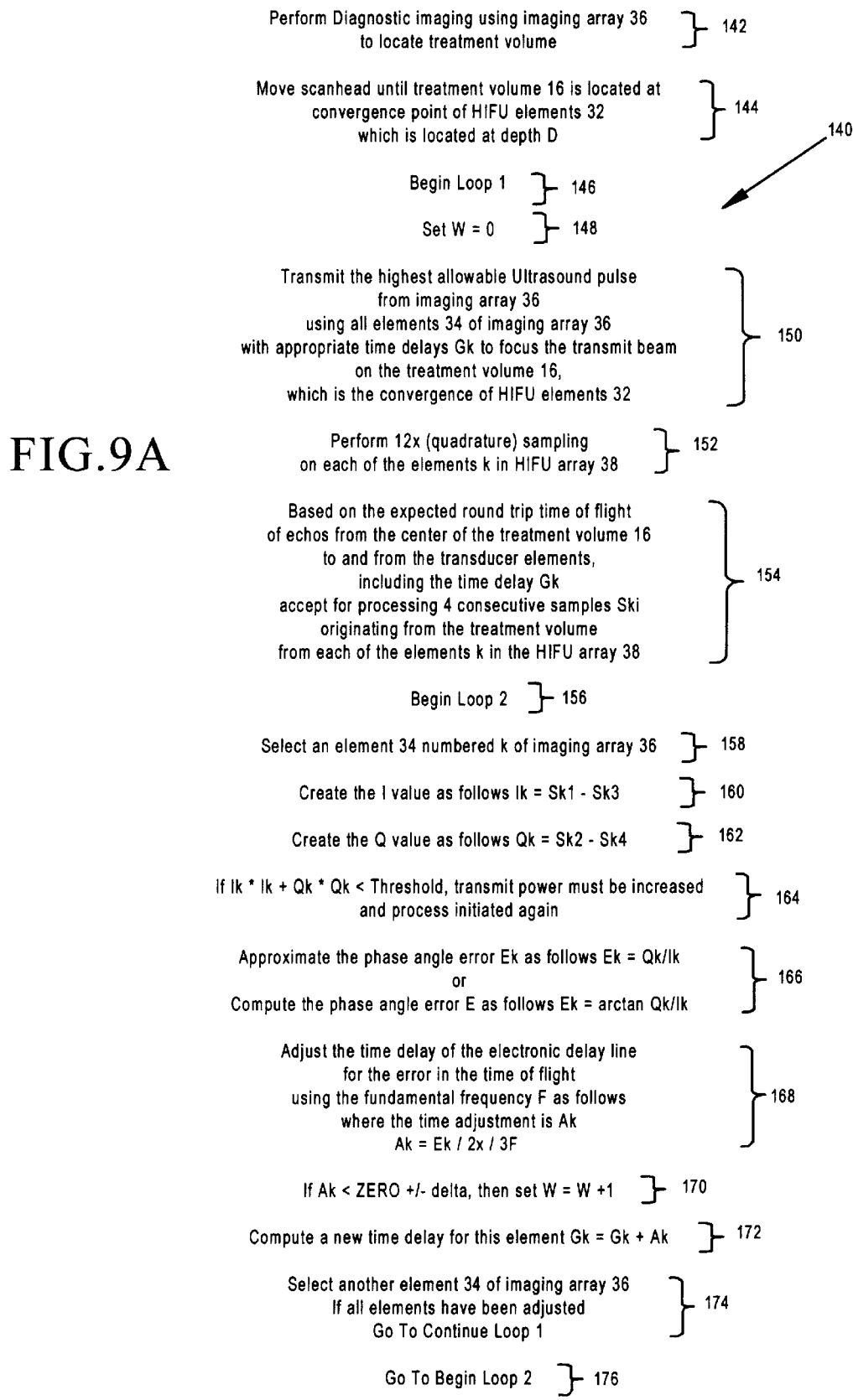

FIG. 8 shows a high level flow chart 80 for an embodiment of the method of this invention. FIGS. 9A–B show a more detailed flow chart for a similar embodiment. Referring to FIG. 8, at one step 82, diagnostic imaging is performed to identify and locate a treatment volume to be treated with HIFU energy. In doing so, diagnostic ultrasound pulses are transmitted from the imaging array portion 36 of the transducer array 12. The reflected ultrasound energy then is processed to view an image of the patient. An operator moves the transducer 12 and adjusts the focus or steering of the imaging array portion 36 to locate the desired treatment volume 16. At another step 84 a focused ultrasound beam is transmitted into the patient through a first aperture including at least the imaging array portion 36 of the transducer array 12. In one embodiment the beam is transmitted as a burst at a prescribed frequency for less than 5 microseconds in duration, resulting in a moderate intensity beam, (e.g., 1–20 W/cm$^2$ SPTP, where SPTP means Spatial Peak Temporal Peak). The prescribed frequency is within the ultrasound frequency range and varies according to the application. The specific frequency is selected for the specific organ or tissue type being treated.

Figure 1A:
FIGS. 1A–C are waveforms of a 1 MHz ultrasound signal at differing intensities exemplifying SPCW amplitude, SPTP amplitude and SPTA amplitude.
Figure 1B:
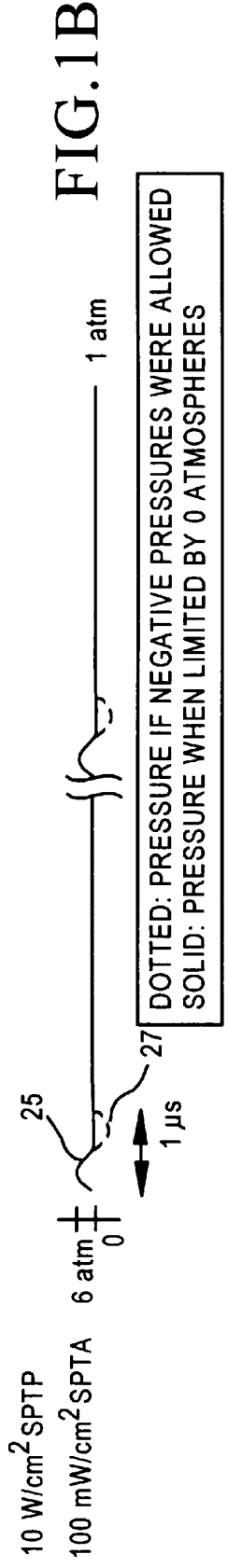
Figure 1C:
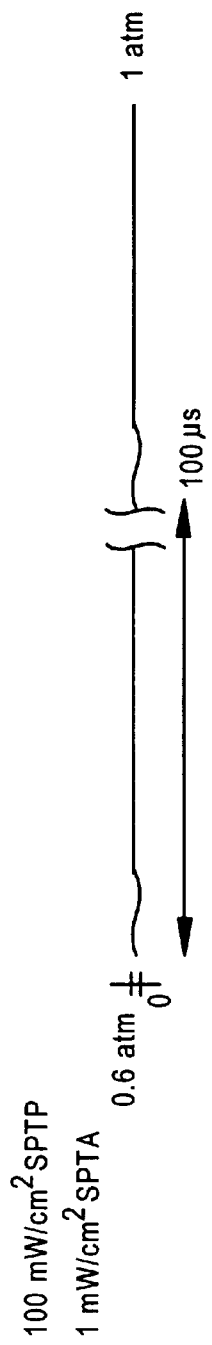

A moderate intensity beam is used for the calibration step because a low intensity beam, such as used for the imaging step will not cause the desired harmonic generation in the focus zone that occurs using a moderate or high intensity ultrasound beam. Moderate intensity as used herein means intensities at which the relationship between molecular velocity fluctuations and the pressure fluctuations within the tissue is nonlinear. Preferably the moderate intensity is chosen to generate harmonics only at the focus of the ultrasound beam. For an imaging application a high conventional ultrasound pulse intensity is up to 10 W/cm$^2$ SPTP. At a decreased conventional imaging intensity of 100 mW/cm$^2$ SPTP, the sinusoidal pressure fluctuation occurring in tissue is approximately 0.6 atmospheres (see waveform 29 of FIG. 1C). Thus, the highest instantaneous pressure in tissue is between 0.4 atm and 1.6 atm. A linear relationship therefore exists between molecular velocity fluctuations and pressure fluctuation. This is desirable for accurately imaging a treatment volume. At the threshold imaging intensity (i.e., 300 mW/cm$^2$ SPTP), the sinusoidal pressure fluctuation occurring in tissue is approximately 1.0 atmospheres. Thus, the highest instantaneous pressure in tissue is between 0.0 atm and 2.0 atm. Thus, a linear relationship still exists between molecular velocity fluctuations and pressure fluctuation.

According to an aspect of this invention, the calibration is performed with a beam having an intensity outside such linear range in the focal zone even in the presence of superficial attenuation so as to benefit from the nonlinear response. The moderate intensity beam used initially is the highest intensity available using the imaging array elements 34. In later iterations during the calibration, the transducer elements 34 and 0 or more HIFU elements 32 define an aperture emitting ultrasound energy forming a beam of moderate power intensity. An aberration will occur at such power level, so the delay lines 24 are adjusted to correct for such aberration (see step 92).

In an exemplary embodiment an attenuation derated spatial peak temporal peak intensity of approximately 10,000 mW/cm$^2$ SPTP is the moderate power intensity achieved, (i.e., about the highest ultrasound pulse intensities used for diagnostic imaging and about 100 times less than HIFU (CW) pulse intensities). At such intensity the thermal and mechanical effects upon a patient are substantially less than for HIFU treatment. At the lower 300 mW/cm$^2$ intensity discussed above, the pressure variation is 1.0 atm. and the highest instantaneous pressure is between 0.0 atm and 2.0 atm. Further increases in intensity cannot drive the lower limit negative. As a result, at higher intensities (such as the moderate intensity beam of step 84) the pressure wave becomes clipped, introducing a harmonic, including the specific harmonic (e.g., the third harmonic) into the pressure fluctuations. For such higher intensity pulses (e.g., 10,000 mW/cm$^2$ SPTP), echoes from the lower intensity regions will contain only the fundamental frequency, whereas echoes from the high intensity regions will contain the fundamental frequency and the specific harmonic frequency. The reflected echoes from the treatment volume act as a point source reflecting a nonlinear ultrasound burst (at the fundamental frequency and harmonics) to both the imaging elements 34 and the HIFU elements 32. Presence of the specific harmonic allows for measurement of the propagation time from the treatment volume. In particular the nonlinear response is used as a signature to identify delay time for echoes received at the various HIFU transducer elements 32 and imaging transducer elements 34.

Accordingly, there is a threshold intensity level of the applied ultrasound energy, above which a relationship between the molecular velocity fluctuations and the pressure fluctuations becomes nonlinear. Such nonlinearity is used to estimate the propagation time for ultrasound pulses transmitted from respective imaging ultrasound elements 34 and received as echoes at HIFU transducer elements 32. In particular, the echo at the specific harmonic of an ultrasound pulse of moderate intensity (e.g., 10 W/cm$^2$ SPTP) and less than HIFU intensity (1000 W/cm$^2$ SPCW), is used to estimate the propagation path transit time for each HIFU transducer element 32 that will converge in a treatment volume 16 through nonhomogeneous tissue. The moderate intensity level 10 W/cm$^2$ SPTP is not enough to perform HIFU. Because the 10 W/cm$^2$ intensity is outside the linear region between molecular velocity fluctuations and pressure fluctuations, third harmonic echoes are distributed in all directions from the treatment volume. These third harmonics echoes have a constant phase angle as the angle of scattering is varied for each radial value (using a spherical coordinate system centered on the target volume). The phase errors in this spherically expanding wavefront are of interest. Specifically, the temporal delay in the specific harmonic echoes, such as the third harmonic echoes, observed by each given transducer element 32 serves as a measure of the propagation path transit time to transmit a pulse that will converge on the treatment volume 16.

At step 86, echoes of the transmitted beam are received in a second aperture including at least at the HIFU array portion 38. Due to the nonlinear relationship between molecular velocity fluctuations and pressure fluctuations, the echoes include ultrasound energy at the prescribed frequency and at a specific harmonic of the prescribed frequency, such as the third harmonic. The specific harmonic echoes are of interest for determining phase advancement.

The specific harmonic echo resulting from the harmonic conversion in the target volume due to the moderate intensity beam is used to measure the relative propagation time for each HIFU transducer element 32. For embodiments in which the elements 32 and 34 are used during a HIFU treatment, the propagation time is determined for each element 34 also. At step 88, the quadrature pairs of the echoes are tested for phase error in the specific harmonic frequency, (e.g., third harmonic frequency). If there is no error, then HIFU treatment can commence (see step 90). If there is an error, then at step 92 the delay lines 24 of the individual transducer elements 32, 34 are adjusted to offset dispersion effects of the nonhomogeneous tissue. More specifically, the phase of each HIFU transducer element 32 and imaging transducer element 34 are adjusted to compensate for phase change introduced by differing tissue along a path towards the treatment volume. Another cycle of the time calibration then commences with the reperformance of steps 84–92 until there is no phase error as determined at step 90.

A time calibrated phase-inverted signal then is used for transmitting the high intensity focussed ultrasound to the desired treatment volume. Thus, while phase inversion is applied, ultrasound energy is transmitted at step 94 from at least the HIFU array portion 38 to the treatment volume 16 at a HIFU intensity for achieving desired ultrasonic medical therapy of the treatment volume. Preferably a narrow band transmit burst is used to achieve the desired harmonics at the treatment volume. The HIFU intensity is greater than the moderate intensity applied at step 84, (e.g., the HIFU intensity is greater than 10 W/cm$^2$ SPTP). In one embodiment the HIFU intensity is at least 500 W/cm$^2$ SPCW. In an exemplary liver treatment application, a HIFU intensity of 1000 W/cm$^2$ SPCW was used (see waveform 21 of FIG. 1A). For an application as shown in FIG. 7, select elements 32 of the HIFU array portion 38 overlaying a patient's ribs are deactivated while step 96 is performed to avoid bone heating, without degrading the effectiveness of other transducer elements 32 emitting ultrasound toward the treatment volume 16. According to preferred embodiments the pitch between transducer elements 32 is prescribed to be fine enough to avoid phase aliasing and may be finer than the spatial frequency of undulations of subcutaneous fat. At step 98, echoes of the HIFU beam are received at imaging elements 34 using harmonic bandpass filtering so as to monitor the HIFU treatment.

Figure 10:
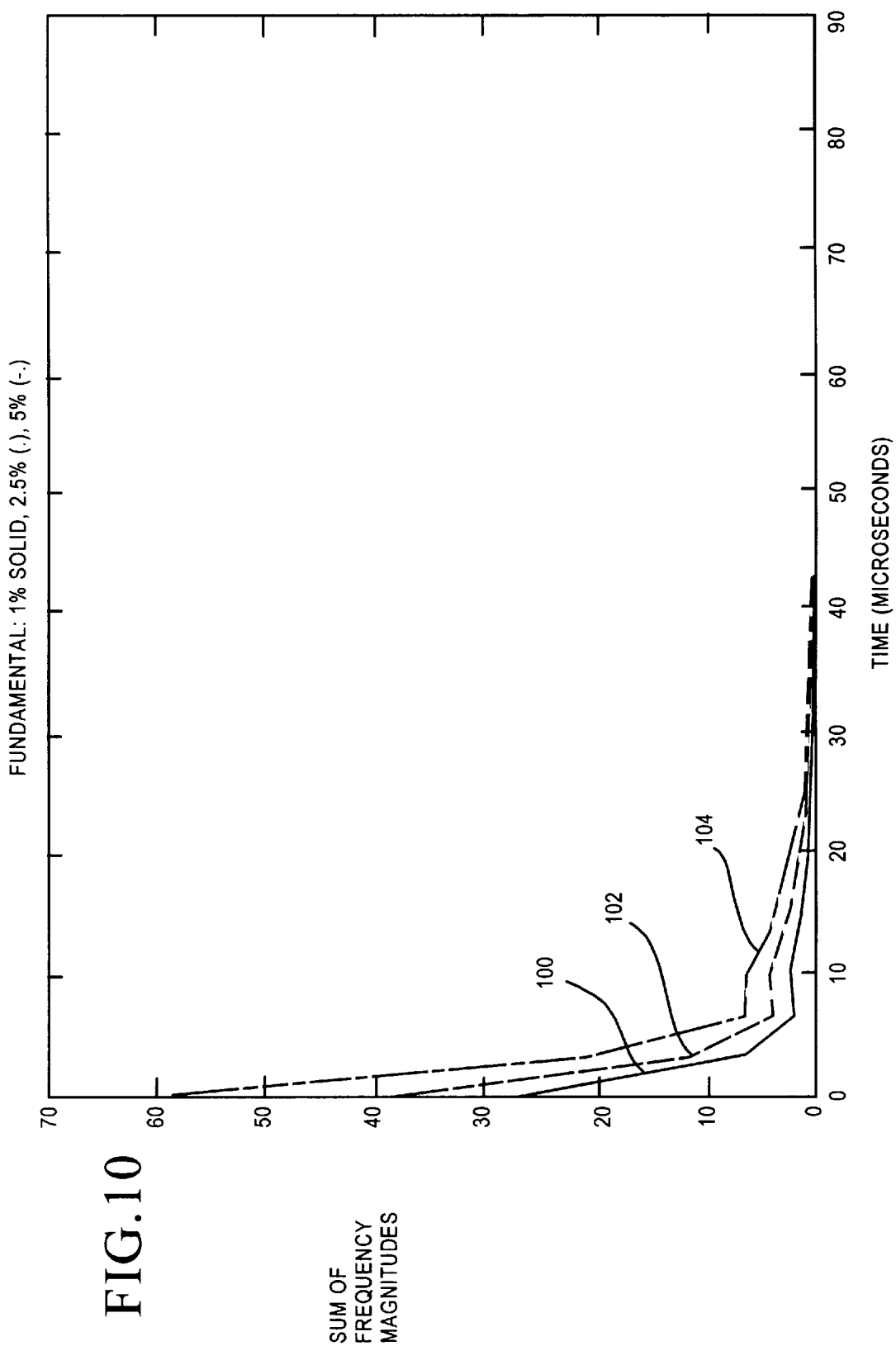
FIG. 10 is a diagram of echo signal frequency magnitudes over time for a transmit signal having a prescribed frequency (three cases are shown for three different intensities of the transmit signal)
Figure 11:
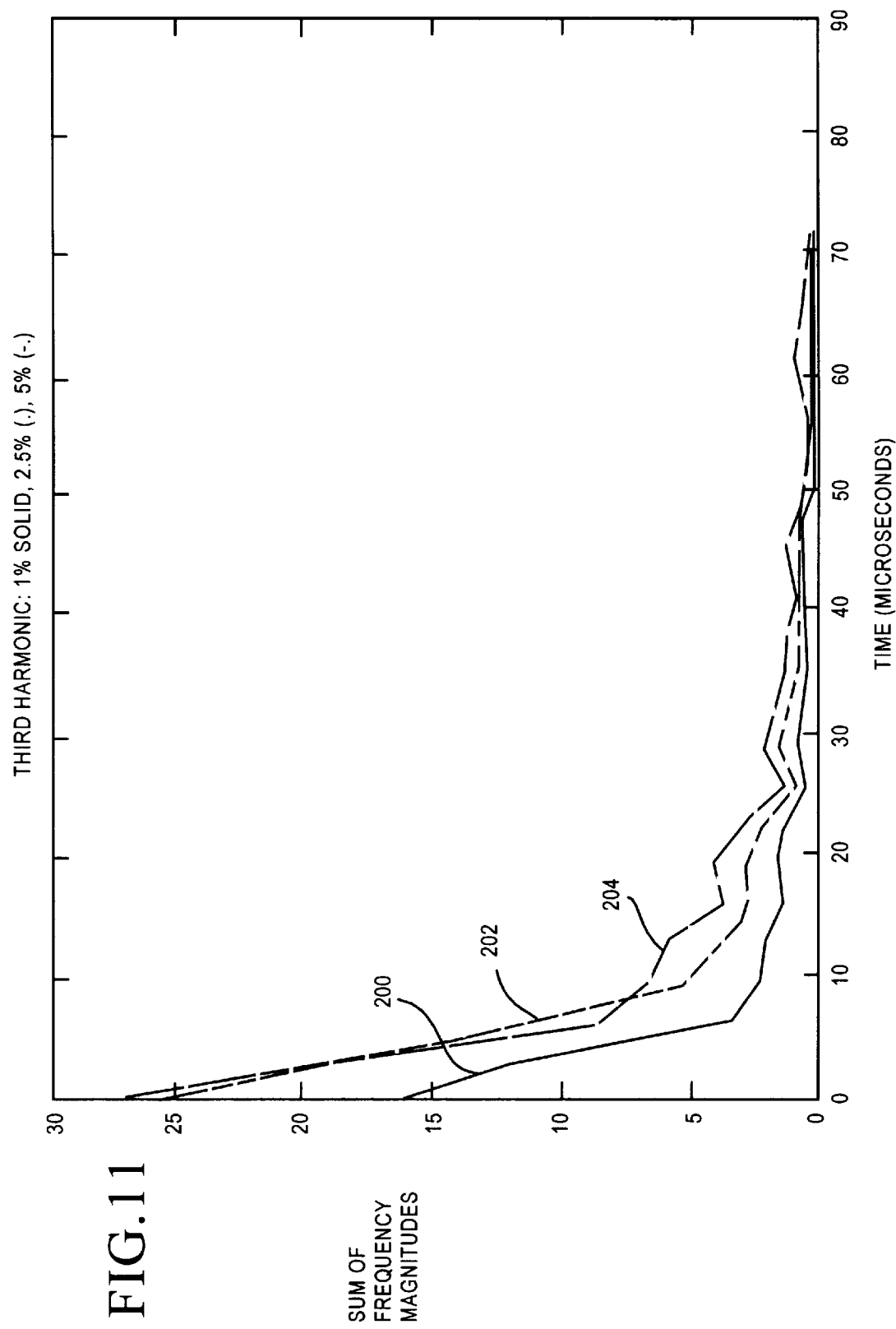
FIG. 11 is a diagram of third harmonic frequency magnitudes over time for the same transmit signals.
Figure 12:
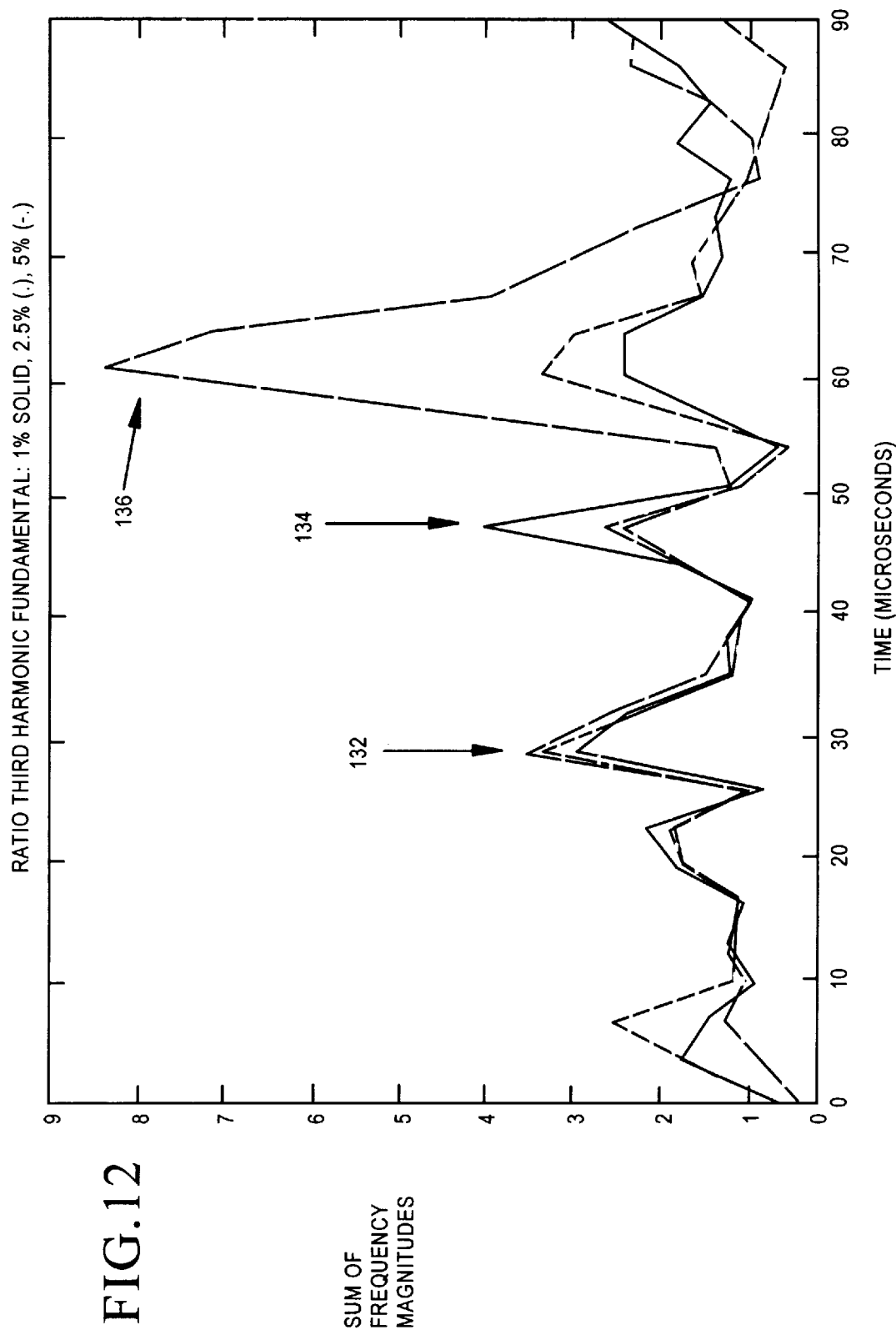
FIG. 12 is a diagram of the ratio of the curves in FIGS. 10 and 11.

FIG. 10 shows waveforms 100, 102, 104 which represent the echo of transmitted ultrasound pulses at an exemplary prescribed frequency of 0.95 MHz. Each waveform corresponds to a transmit signal at a different intensity. As expected the echo drops off due to attenuation over time, wherein time corresponds to depth of reflection within the phantom. FIG. 11 shows waveforms 200, 202, 204 which are the third harmonic frequency (e.g., 2.85 MHz for the 0.95 MHz exemplary fundamental frequency) responses corresponding to the pulses of waveforms 100, 102, 104. FIG. 12 shows the ratio of the corresponding waveforms in FIGS. 10 and 11 (i.e., the third harmonic magnitudes relative to the fundamental frequency magnitudes). Referring to FIG. 12, a first peak 132 at 30 microseconds echo delay corresponds to a 23 mm depth. A second peak 134 at 47 microseconds echo delay corresponds to 36 mm depth. A third peak 136 at 62 microseconds echo delay corresponds to 48 mm depth. Peaks 132, 134 are locations in which near field peaks for the fundamental frequency and third harmonic frequency overlap. At the peak 136 the third harmonic echo from the highest intensity is much greater than the similar ratios for the other depths and from the lower transmit intensities. The depth 48 mm for such peak 136 corresponds to the design focal depth (i.e., the treatment depth). Phase delay of one or more elements 32 of the HWU array portion 38 and imaging elements 34 of imaging array portion 36 are adjusted to alter the depth at which such maximum peak occurs (see step 92). The depth of the maximum peak is to be adjusted to the depth of the treatment volume to be treated.

Referring to FIGS. 9A–B, the method is described in more detail. At one step 142 diagnostic imaging is performed using the imaging array 36 to locate the treatment volume 16. At step 144 the transducer probe scanhead is moved until the treatment volume 16 is located at a convergence point of HIFU array elements 32 at some depth D.

At step 146 a first loop begins. At step 148 a variable W is set to 0. At step 150 an ultrasound pulse is transmitted from the imaging array 36 to focus the transmit beam on the treatment volume 16. This is also the convergence point of the HIFU elements 32. At step 152 quadrature sampling is performed on each element 34i of imaging array 36. At step 154 four consecutive samples originating from the treatment volume 16 are processed for each element 34i. Such samples are selected based upon the expected round trip time from a respective element 34i to the center of the treatment volume 16 and back, including any time delay included at a corresponding delay line 24. At step 156 a second processing loop within the first processing loop begins.

At step 158 data for an element 34i is selected for processing. At step 160 the in phase component I is derived for the element 34i by subtracting the third sample value from the first sample value. At step 162 the quadrature component Q is derived for the element 34i by subtracting the fourth sample value from the second sample value. At step 164, the results are tested to see if the threshold intensity has been exceeded. If the in phase component times the in phase component, plus the quadrature phase component times the quadrature component is less than the threshold intensity, then transmit power is increased and the process initiated again at the start of loop 1. Otherwise at step 166 phase angle error, E, is approximated as the quadrature component value divided by the in phase component value or as the arc tangent of the quadrature component value divided by the in phase component value. At step 168 the time delay for the element 34i is adjusted using the corresponding delay line 24 for the error in the time of flight using the fundamental frequency F. The time adjustment is the phase angle error for such element 34i divided by the quotient 2 pi over 3 times the fundamental frequency. At step 170 the adjustment is test. If the adjustment is less than zero plus or minus some delta value, then the variable W is incremented. At step 172 a new time delay is derived for the element 34i by adding the adjustment to the prior value of the time delay for such element 34i. At step 174 another element 34(i+1) is selected for processing. If all elements 34 have been processed then processing jumps to step 178, otherwise processing goes back to the beginning of the second loop (step 156) to process the next element 34(i+1).

At step 178 the first loop's processing continues. At step 180, W is tested to determine that is zero. If not 0 then processing goes to the beginning of loop 1 (step 146). If W=0, then at step 182 an ultrasound pulse is transmitted from the imaging array 36 and one or more elements 32 of the HIFU array 38. At step 184 quadrature sampling is performed on each element 32i of the HIFU array 38. At step 186 four consecutive samples originating from the treatment volume 16 are processed for each element 32i. Such samples are selected based upon the expected round trip time from a respective element 32i to the center of the treatment volume 16 and back to the element 32i, including any time delay, G, included at a corresponding delay line 24. At step 188 another processing loop (i.e., loop 3) within the first processing loop begins.

At step 190 data for an element 32i is selected for processing. At step 192 the in phase component I is derived for the element 32i by subtracting the third sample value from the first sample value. At step 194 the quadrature component Q is derived for the element 32i by subtracting the fourth sample value from the second sample value. At step 196, the results are tested to see if the threshold intensity has been exceeded. If the in phase component times the in phase component, plus the quadrature phase component times the quadrature component is less than the threshold intensity, then transmit power is increased and the process initiated again at the start of loop 1. Otherwise at step 198 phase angle error, E, for such element 32i is approximated as the quadrature component value divided by the in phase component value or as the arc tangent of the quadrature component value divided by the in phase component value. At step 200 the time delay for the element 32i is adjusted using the corresponding delay line 24 for the error in the time of flight using the fundamental frequency F. The time adjustment is the phase angle error for such element 34i divided by the quotient 2 pi over 3 times the fundamental frequency. At step 202 a new time delay is derived for the element 32i by adding the adjustment to the prior value of the time delay for such element 32i. At step 204 another element 32(i+1) is selected for processing. If all elements 32 have been processed then processing jumps to step 208, otherwise at step 206 processing goes back to the beginning of the loop 3 (step 188) to process the next element 32(i+1). At step 208 the focussing is complete. At step 210 a HIFU burst then is emitted to perform HIFU therapy on the treatment volume 16.

Meritorious and Advantageous Effects

According to one advantage of the invention, HIFU pulses are transmitted through nonhomogeneous tissue without adversely heating tissue in the path between the ultrasound transducer and the treatment volume. Thus, treatment volumes can be treated to achieve hyperthermia, superthermia, ultrathermia or cavitation without adversely impacting intervening tissue.

Although a preferred embodiment of the invention has been illustrated and described, various alternatives, modifications and equivalents may be used. For example although a system in which each transducer element has a corresponding transmitter and receiver is described, in an alternative embodiment there is one transmitter which generates multiple drive signals for the respective transducer array elements. Although a preferred embodiment of the method has been described for focussing a HIFU ultrasound burst upon a treatment volume, the method also may be applied for focussing a diagnostic imaging ultrasound burst or beam at a target volume. Also, although in the preferred embodiment an imaging array and a HIFU array are shown and described, the method also may be implemented using merely one imaging transducer element and/or only one HIFU transducer element. Therefore, the foregoing description should not be taken as limiting the scope of the inventions which are defined by the appended claims.

What is claimed is:

1. A method for applying ultrasound energy through a nonhomogeneous mass to an identified treatment volume to provide ultrasonic therapy to the treatment volume, wherein application of ultrasound energy causes molecular velocity fluctuation and pressure fluctuation along a path from a source of ultrasound energy to the treatment volume, and wherein there is a threshold intensity level at the treatment volume of the applied ultrasound energy, above which a relationship between the molecular velocity fluctuations and the pressure fluctuations becomes nonlinear in the treatment volume, the method comprising the steps of:

configuring a first transducer array to define a first aperture, wherein the first transducer array is formed by a plurality of transducer elements;

while the first transducer array is configured to define the first aperture, transmitting a pulse of ultrasound energy from the first transducer array toward the treatment volume at a prescribed frequency and at a first peak intensity greater than the threshold intensity level at the treatment volume;

receiving echoes of the transmitted ultrasound energy at the first transducer array and at a second transducer array, the second transducer array having a plurality of transducer elements, wherein the echoes include ultrasound energy at a specific harmonic of the prescribed frequency;

for echoes received during an expected time window for receiving echoes from the treatment volume, comparing arrival time phase of the received echoes at the specific harmonic for each active element of the first transducer array and the second transducer array;

adjusting phase delay for received echoes for one or more elements of the second transducer array to achieve phase inversion; and while phase inversion is applied to the second transducer array, transmitting ultrasound energy from the second transducer array to the treatment volume at a second intensity for achieving desired ultrasonic medical therapy of the treatment volume, wherein the second intensity at the treatment volume is greater than the first peak intensity at the treatment volume.

2. The method of claim 1, wherein the steps of transmitting, receiving and comparing are repeated until each active element of the second transducer array is optimally aimed at the treatment volume.

3. The method of claim 1, wherein the step of transmitting from the first ultrasound transducer array comprises emitting a pulse of less than 10 microseconds in duration.

4. The method of claim 1, wherein the first peak intensity is at least 500 mW/cm$^2$ SPTP.

5. The method of claim 1, wherein the first intensity is greater than 500 mW/cm$^2$ SPTP and the second intensity is at least 50 W/cm$^2$ SPTP.

6. The method of claim 1 applied to a patient, wherein the treatment volume is in an organ, and further comprising prior to the step of transmitting from the first transducer array, the steps of:

measuring amplitude of the received echoes;

deactivating first elements of the first transducer array which receive echoes having an amplitude less than a threshold amplitude, wherein the threshold amplitude serves to identify ultrasound-obstructed pathways; and deactivating second elements of the second transducer array which receive echoes having an amplitude less than the threshold amplitude.

7. A method for applying ultrasound energy through a nonhomogeneous path to an identified treatment volume to provide ultrasonic therapy to the treatment volume, wherein application of ultrasound energy causes molecular velocity fluctuation and pressure fluctuation along a path from a source of ultrasound energy to the treatment volume, and wherein there is a threshold intensity level of the applied ultrasound energy at the treatment volume, above which a relationship between the molecular velocity fluctuations and the pressure fluctuations becomes nonlinear, the method comprising the steps of:

configuring a transducer array to define a first aperture, wherein the first transducer array is formed by a first plurality of imaging elements and a second plurality of treatment elements, the treatment elements capable of transmitting higher ultrasound power than the imaging elements, and wherein the first aperture includes at least multiple ones of the first plurality of imaging elements;

while the transducer array is configured to define the first aperture, transmitting a burst of ultrasound energy for a prescribed time from the transducer array toward the treatment volume at a prescribed frequency and at a first peak intensity greater than the threshold intensity at the treatment volume;

configuring the transducer array to define a second first aperture, wherein the second aperture includes at least multiple ones of the first plurality of imaging elements and multiple ones of the second plurality of treatment elements;

while the transducer array is configured to define the second aperture, receiving echoes of the transmitted ultrasound energy at the transducer array, wherein the echoes include ultrasound energy at harmonics of the prescribed frequency;

for echoes received during an expected time window for receiving echoes from the treatment volume, comparing arrival time phase of the received echoes at the prescribed frequency and the specific harmonic of the prescribed frequency for each active element of the transducer array;

adjusting phase delay for the received echoes for one or more of said elements of the transducer array to achieve phase inversion;

configuring the transducer array to define a third aperture, wherein the third aperture includes at least multiple ones of the second plurality of treatment elements; and while phase inversion is applied to the transducer array, transmitting an ultrasound burst from the transducer array through the third aperture to the treatment volume, wherein the ultrasound burst is of a second peak intensity at the treatment volume for achieving desired ultrasonic medical therapy of the treatment volume, wherein the second peak intensity at the treatment volume is greater than the first peak intensity at the treatment volume.

8. The method of claim 7, wherein the steps of configuring a first aperture, transmitting, configuring a second aperture, receiving and comparing are repeated until each active element of the second transducer array is optimally aimed at the treatment volume.

9. The method of claim 7, wherein the step of transmitting from the ultrasound transducer array comprises emitting a pulse of less than 10 microseconds in duration.

10. The method of claim 7, wherein the first peak intensity is at least 500 mW/cm$^2$ SPTP.

11. The method of claim 7, wherein the first peak intensity is greater than 500 mW/cm$^2$ SPTP and the second peak intensity is at least 50 W/cm$^2$ SPTP.

12. The method of claim 7, applied to a patient, wherein the treatment volume is an organ, and further comprising prior to the step of transmitting from the transducer array, the steps of:

measuring amplitude of the received echoes;

deactivating elements of the transducer array which receive echoes having an amplitude less than a threshold amplitude, wherein the threshold amplitude serves to identify ultrasound-obstructed pathways.

13. An ultrasound system for applying ultrasound energy through a nonhomogeneous path to a treatment volume to provide ultrasonic therapy to the treatment volume, wherein application of ultrasound energy causes molecular velocity fluctuation and pressure fluctuation along a path from a source of ultrasound energy to the treatment volume, and wherein there is a threshold intensity level of the applied ultrasound energy at the treatment volume, above which a relationship between the molecular velocity fluctuations and the pressure fluctuations becomes nonlinear, the apparatus comprising:

a first transducer array configured to define a first aperture, the first transducer array having a plurality of transducer elements which transmit ultrasound energy at a prescribed frequency and at a first peak intensity greater than the threshold intensity at the treatment volume, the first aperture being formed by active elements of the first transducer array;

a second transducer array having a plurality of active transducer elements which receive echoes of the transmitted ultrasound energy at a specific harmonic of the prescribed frequency;

means for comparing phase of the echoes at the specific harmonic for each active element of the first transducer array and the second transducer array by measuring transit time for the transmitted ultrasound energy to propagate from the first transducer array to the treatment volume and echo back to the second transducer array while the second transducer array is aimed at the treatment volume; and means for adjusting the phase of received echoes for one or more elements of the second transducer array so that each active element of the second transducer array is aimed at the treatment volume, wherein propagation transit time is applied as an advance time to each active element of the second transducer array to achieve phase inversion; and wherein while phase inversion is applied to the second transducer array, ultrasound energy is transmitted from the second transducer array to the treatment volume at a second peak intensity for achieving desired ultrasonic medical therapy of the treatment volume, wherein the second peak intensity is greater than the first peak intensity at the treatment volume.

14. The system of claim 13, wherein a transmission of ultrasound energy from the first ultrasound transducer array comprises a pulse of less than 10 microseconds in duration.

15. The system of claim 13, wherein the first peak intensity is at least than 500 mW/cm$^2$ and the second peak intensity is at least 50 W/cm$^2$ SPTP.

16. The system of claim 13, further comprising a plurality of time delay lines coupled to the transducer array, each of the time delay lines being adjustable to introduce a select time delay for the transmission at a corresponding transducer element of the transducer array, and wherein the phase adjusting means adjusts the time delay of at least one time delay line to adjust the phase of the received echoes.

17. An ultrasound system for applying ultrasound energy through a nonhomogeneous path to a treatment volume to provide ultrasonic therapy to the treatment volume, wherein application of ultrasound energy causes molecular velocity fluctuation and pressure fluctuation along a path from a source of ultrasound energy to the treatment volume, and wherein there is a threshold intensity level of the applied ultrasound energy at the treatment volume, above which a relationship between the molecular velocity fluctuations and the pressure fluctuations becomes nonlinear at the treatment volume, the apparatus comprising:

a transducer array including a first plurality of imaging elements and a second plurality of treatment elements, the treatment elements capable of transmitting higher ultrasound power than the imaging elements;

a plurality of time delay lines coupled to the transducer array, each one of the plurality time delay lines being adjustable to introduce a select time delay respectively for transmission and reception at a corresponding transducer element;

means for defining a first aperture of the transducer array through which a burst of ultrasound energy is transmitted toward the treatment volume for a prescribed time at a prescribed frequency and at a first peak intensity greater than the threshold intensity at the treatment volume, the first aperture including at least multiple ones of the first plurality of imaging elements;

means for defining a second aperture of the transducer array through which echoes of the transmitted ultrasound energy are received, wherein the echoes include ultrasound energy at harmonics of the prescribed frequency, the second aperture including at least multiple ones of the first plurality of imaging elements and multiple ones of the second plurality of treatment elements;

means for testing for time error of the echoes at the prescribed frequency and the specific harmonic of the prescribed frequency;

means for reducing time error by adjusting respective time delay at the plurality of time delay lines to achieve phase inversion and aim the transducer array at the treatment volume; and wherein while phase inversion is applied to the second transducer array, ultrasound energy is transmitted through a third aperture of the transducer array to the treatment volume at a second peak intensity at the treatment volume for achieving desired ultrasonic medical therapy of the treatment volume, wherein the second peak intensity is greater than the first peak intensity at the treatment volume, and wherein the third aperture includes at least multiple ones of the second plurality of treatment elements.

18. The system of claim 17, further comprising means for measuring propagation transit time for the ultrasound energy to propagate from the transducer array to the treatment volume and echo back to the transducer array, and wherein adjustment of respective time delay is achieved by applying the propagation transit times an advance time for each element of the transducer array.

19. The system of claim 17, wherein a transmission of ultrasound energy from the first ultrasound transducer array comprises a pulse of less than 10 microseconds in duration.

20. The system of claim 17, wherein the first intensity is at least 500 mW/cm$^2$ SPTP and the second intensity is at least 50 W/cm$^2$ SPTP.

21. A method for applying ultrasound energy through a nonhomogeneous mass to an identified treatment volume to provide ultrasonic therapy to the treatment volume, wherein application of ultrasound energy causes molecular velocity fluctuation and pressure fluctuation along a path from a source of ultrasound energy to the treatment volume, and wherein there is a threshold intensity level at the treatment volume of the applied ultrasound energy, above which a relationship between the molecular velocity fluctuations and the pressure fluctuations becomes nonlinear in the treatment volume, the method comprising the steps of:

transmitting a pulse of ultrasound energy from a first transducer toward the treatment volume at a prescribed frequency and at a first peak intensity greater than the threshold intensity level at the treatment volume;

receiving echoes of the transmitted ultrasound energy at the first transducer and at a second transducer, wherein the echoes include ultrasound energy at a specific harmonic of the prescribed frequency;

for echoes received during an expected time window for receiving echoes from the treatment volume, comparing arrival time phase of the received echoes at the specific harmonic for the first transducer and comparing arrival time phase of the received echoes at the specific harmonic for the second transducer;

adjusting phase delay of received echoes for the second transducer to achieve phase inversion; and while phase inversion is applied to the second transducer, transmitting ultrasound energy from the second transducer to the treatment volume at a second intensity for achieving desired ultrasonic medical therapy of the treatment volume, wherein the second intensity at the treatment volume is greater than the first peak intensity at the treatment volume.

22. A method for focussing ultrasound energy through a nonhomogeneous mass to a treatment volume, the method comprising the steps of:

transmitting a pulse of ultrasound energy from a transducer toward the treatment volume;

receiving echoes of the transmitted ultrasound energy at the transducer, wherein the echoes include ultrasound energy at a specific harmonic of the prescribed frequency;

for echoes received during an expected time window for receiving echoes from the treatment volume, comparing arrival time phase of the received echoes at the specific harmonic;

adjusting phase delay of received echoes for the transducer to achieve phase inversion; and while phase inversion is applied to the transducer, transmitting ultrasound energy from the transducer to the treatment volume.

23. The method of claim 22, further comprising the step of receiving echoes of the ultrasound energy while phase inversion is applied to perform medical diagnostic ultrasound imaging.

24. The method of claim 22, wherein the transmitting ultrasound energy to the treatment volume while phase inversion is applied is for achieving ultrasonic medical therapy of the treatment volume in which application of the ultrasound energy causes molecular velocity fluctuation and pressure fluctuation along a path from the transducer to the treatment volume, and wherein there is a threshold intensity level of the applied ultrasound energy at the treatment volume, above which a relationship between the molecular velocity fluctuations and the pressure fluctuations becomes nonlinear in the treatment volume.

25. An ultrasound system for applying ultrasound energy through a nonhomogeneous path to a treatment volume to provide ultrasonic therapy to the treatment volume, wherein application of ultrasound energy causes molecular velocity fluctuation and pressure fluctuation along a path from a source of ultrasound energy to the treatment volume, and wherein there is a threshold intensity level of the applied ultrasound energy at the treatment volume, above which a relationship between the molecular velocity fluctuations and the pressure fluctuations becomes nonlinear, the apparatus comprising:

a first transducer which transmits ultrasound energy at a prescribed frequency and at a first peak intensity greater than the threshold intensity at the treatment volume, the transducer and a second transducer receiving echoes of the transmitted ultrasound energy at a specific harmonic of the prescribed frequency;

means for comparing phase of the echoes at the specific harmonic for the first transducer by measuring transit time for the transmitted ultrasound energy to propagate from the first transducer to the treatment volume and echo back to the first transducer;

means for comparing phase of the echoes at the specific harmonic for the second transducer by measuring transit time for the transmitted ultrasound energy to propagate from the first transducer to the treatment volume and echo back to the second transducer;

means for adjusting the phase of received echoes for the second transducer so that the transducer is aimed at the treatment volume, wherein propagation transit time is applied as an advance time to the second transducer to achieve phase inversion; and wherein while phase inversion is applied to the second transducer, ultrasound energy is transmitted from the second transducer to the treatment volume at a second peak intensity for achieving desired ultrasonic medical therapy of the treatment volume, wherein the second peak intensity is greater than the first peak intensity at the treatment volume.

* * * * *